(12) United States Patent
Ales et al.

(10) Patent No.: US 8,383,127 B2
(45) Date of Patent: Feb. 26, 2013

(54) **POLYSACCHARIDE EXTRACT OF *LENTINUS* AND PHARMACEUTICAL, COSMETIC OR NUTRACEUTICAL COMPOSITIONS COMPRISING SUCH AN EXTRACT**

(75) Inventors: Patrick Ales, Paris (FR); Alexandre Escaut, Boulogne (FR); Pierre Escaut, legal representative, Paris (FR); Jean-Christophe Choulot, Rambouillet (FR)

(73) Assignee: Caster, Paris (FR)

( * ) Notice: Subject to any disclaimer, the term of this patent is extended or adjusted under 35 U.S.C. 154(b) by 623 days.

(21) Appl. No.: 12/175,064

(22) Filed: Jul. 17, 2008

(65) Prior Publication Data

US 2009/0270343 A1    Oct. 29, 2009

(30) Foreign Application Priority Data

Jul. 20, 2007 (FR) ...................... 07 56641

(51) Int. Cl.
*A61K 36/06* (2006.01)
*A61K 31/7004* (2006.01)
*A61K 31/7016* (2006.01)
*A61K 31/702* (2006.01)
*A61K 31/715* (2006.01)

(52) U.S. Cl. ......................... 424/195.15; 514/53; 514/54

(58) Field of Classification Search ............. 424/195.15; 514/53, 54
See application file for complete search history.

(56) References Cited

U.S. PATENT DOCUMENTS 5,997,875 A    12/1999 Zhou et al. ................. 424/195.1

FOREIGN PATENT DOCUMENTS

| EP | 1 389 466 | 2/2004 |
|----|-----------|--------|
| EP | 1 495 753 | 1/2005 |
| FR | 2 829 389 | 3/2003 |
| JP | 62 142120 | 6/1962 |
| KR | 2006 0129630 | 12/2006 |

OTHER PUBLICATIONS

Chihara et al. Cancer Research, 1970, 30, p. 2776-2781.*
Yang et al. Food Chemistry, 2001, 72, p. 465-471.*
Wasser, S.P. Encyclopedia of Dietary Supplements, 2005, Marcel Dekker Inc., p. 653-664.*
Hadj-Rabia et al., "Claudin-1 gene mutations in neonatal sclerosing cholangitis associated with ichthyosis: A tight junction disease," *Gastroenterology*, 127(5):1386-90, 2004; correction in *Gastroenterology*, 128(2):524, 2005.
Prieto et al., "Influence of traditional Chinese anti-inflammatory medicinal plants on leukocyte and platelet functions," *Journal of Pharmacy and Pharmacology*, 55:1275-1282, 2003.
Tsuruta et al., "The barrier function of skin: how to keep a tight lid on water loss," *Trends Cell Biol.*, 12(8):355-7, 2002.
Zheng et al., "Characterization and immunomodulating activities of polysaccharide from *Lentinus edodes*," *International Immunopharmacology*, 5:811-820, 2005.

\* cited by examiner

*Primary Examiner* — Shaojia Anna Jiang
*Assistant Examiner* — Jonathan S Lau
(74) *Attorney, Agent, or Firm* — Fulbright & Jaworski L.L.P.

(57) ABSTRACT

The present invention relates to a polysaccharide extract derived from a mushroom of the *Lentinus* genus and also to the method for preparing such an extract. This polysaccharide-rich extract can be used as a nutraceutical, cosmetic or pharmaceutical preparation.

8 Claims, 7 Drawing Sheets

POLYSACCHARIDE EXTRACT OF LENTINUS AND PHARMACEUTICAL, COSMETIC OR NUTRACEUTICAL COMPOSITIONS COMPRISING SUCH AN EXTRACT

The present invention relates to a polysaccharide extract derived from a mushroom of the *Lentinus* genus and also to the method for preparing such an extract. This polysaccharide-rich extract can be used as a nutraceutical, cosmetic or pharmaceutical preparation.

BACKGROUND OF THE INVENTION

1. Field of the Invention

The skin is an organ in its own right, playing a fundamental role in health and also in the appearance. A barrier which is both resistant and fragile, it undergoes perpetual renewal. Despite this, the first signs of skin ageing manifest themselves discreetly before 30 years of age. With time, the skin loses its suppleness and its ability to retain water decreases. Although dehydration is only one of the aspects of skin ageing, it appears that the water content is closely linked to a number of morphological and molecular characteristics of normal skin.

2. Description of Related Art

The protection against water loss is mainly provided by the epidermis and its horny layer (Verdier-Sevrain., S. & F., Bonte, 2007, J. Cosmet. Dermatol. 6(2): pp 75-82). The epidermis is a stratified squamous epithelium consisting mainly of keratinocytes (90%), the dermis being the connective feeder support for the epidermis, the main biological purpose of which is the formation of the horny layer. The "stratum corneum" or horny layer is the most superficial zone of the epidermis. It consists of a stack of flat anuclear cells, corneocytes, which are the end result of the keratinocyte differentiation and proliferation process. By virtue of its solidity and its compact stratified structure, the stratum corneum ensures a barrier function: it opposes transcutaneous water loss and protects the underlying layers against mechanical and chemical attacks and ultraviolet irradiation.

The water content of the skin is conditioned by various parameters, among which are, inter alia, the degree of water elimination, which depends on the balance which exists between the ability of the skin to retain water and the transepidermal losses due to evaporation, a type of physiological dehydration reflecting the integrity of the epithelial skin barrier and also its functionality.

All epithelia, including that of the skin, comprise cells that are associated with one another with more or less cohesion. Tight junctions are specific to all epithelial tissues. Generally located at the top of the cells, they seal skin epithelial cells to one another and thus prevent the intercellular passage of fluids out of tissues. Their principal function is therefore to ensure the leaktightness of the epidermis and to prevent the organism from losing all its water on contact with the outside environment (Tsuruta, D., et al., 2002, Trends Cell Biol. 12(8): pp 355-7).

The junction between epidermal cells is in fact due to homophilic interactions which involve several adhesion proteins. The first is occludin (from the Latin word occludere=to trap). It is a transmembrane protein having a weight of 64 kDa, comprising a polypeptide chain which crosses the membrane four times. The second is claudin (from the Latin word claudere=to close), a transmembrane protein having a weight of 22 kDa, also comprising a polypeptide chain which crosses the membrane four times. Claudin is part of a family of at least 24 members, several of which may be present in the same junction. The third protein is JAM (junctional adhesion molecule), a protein having a molecular weight of 33 kDa, and the polypeptide chain of which crosses the membrane just once.

Occludin, claudins and JAM assembled form a network of fibrilles which encircle the apical domain of epithelial cells. The tight junctions are bound to intracellular proteins such as ZO-1 and ZO-2 (zonula occludens) which, in turn, are bound to the cytoskeleton (actin). This interaction with the cytoskeleton determines the location of the junction at the apical domain of the cell.

Depending on the expression of the proteins which constitute the tight junctions, the epidermal cells are more or less capable of limiting the permeability of the skin epithelium. The hydration of the skin remains a complex phenomenon which is of essential importance in cosmetology or in dermatology, hence the constant search for new treatments which reprogram the process of deep and surface hydration for replumping the skin from the inside and smoothing out the contours of the skin.

*Lentinus edodes* (shii-take), an edible forest mushroom from Japan, is known in many Asian countries (China, Korea, etc.) to be one of the best mushrooms for its taste and its fragrance. *Lentinus edodes* is in fact characterized by a number of specific substances, for instance guanosine 5'-monophosphate which induces a pleasant fragrance and an aromatic substance, lenthionine.

Hundreds of edible mushrooms currently exist around the world, but the majority are not cultivated. Only a few mushrooms, *Agaricus bisporus* in Europe and *Lentinus edodes* in Asia, are cultivated on a large scale, but *Agaricus bisporus* is cultivated on compost and used fresh, whereas *Lentinus* is cultivated on wood and often dried. This is because the drying of *Lentinus* makes it possible to conserve it, while at the same time preserving its aroma and its taste.

The shii-take is an expensive mushroom which is also known as "elixir of life". According to the great Chinese physician WU SHUI, who lived at the time of the Ming dynasty (1364-1644), the shii-take increases vigour and vitality and is very effective in the preventive treatment of brain haemorrhage. Recently, the medical properties of the shii-take have been studied by Japanese researchers and it has been possible to demonstrate antiviral, antibiotic, antitumour and blood-lipid-lowering actions.

Approximately 800 years ago, the mushroom began to be cultivated in China (the Chinese name for shii-take is HOANG-KO). Today, close to 230 000 small producers of shii-take exist in Japan. This mushroom is also cultivated in Korea and in China and is collected in the wild state in forests in other Asian countries. In 1974, the total production in Japan was 12 000 tonnes of dried mushrooms and 55 000 tonnes of fresh mushrooms. The shii-take is only exported dried.

An aqueous extract of *Lentinus* rich in lentinan is known, from patent FR2776184, for its antitumour properties. Patent FR2829389 describes a method for extracting *Lentinus*, comprising steps of enzymatic hydrolysis in order to obtain an extract capable of inhibiting the activity of certain metalloproteases, MMPs, and in particular MMP-1 and MMP-2.

The chemical composition of the shii-take has been determined by standard analytical methods published by the Analytical Chemistry Association. The quantitative determinations related to water content, crude proteins, fats and ash. The crude proteins were determined relative to the nitrogen contained, assayed by the Kjeldahl method, using the conversion factor (N×6.25). In fact, the studies and assays carried out on the crude protein show that only a part is digestible. Other studies demonstrate that the probable degree of digestibility is 60-70%. This reduced degree is explained by the fact that the mushrooms contain a not insignificant percentage of non-protein nitrogen bound to the chitin of the cell walls. It can therefore be considered that the conversion factor is 70% N×6.25 or (N×4.38).

The percentage of fat contained in the mushrooms can range between 1% and 15%-20% of the dry weight. On average, the mushrooms contain 2% to 8% of fats and all the lipid categories are found therein, such as free fatty acids (stearic acid, oleic acid, palmitic acid and linoleic acid), mono-, di- and triglycerides, sterols (ergosterol), sterol esters and phospholipids. The fats have been analysed by extraction with solvents; the fibre, as residue after digestion; the ash as residue after incineration. The fresh mushrooms contain between 3% and 28% of carbohydrates and 3% to 32% of fibre. The carbohydrates have been calculated by difference, as total carbohydrates (fibre included) or as carbohydrates without fibre. It may be considered that the greatest amount of non-protein nitrogen is in the form of chitin and a small amount is in the form of urea or of ammonium salts.

| Sample | Water content | Crude protein N × 4.68 | Fat | Carbohydrates Total | Without N | Fibre | Ash | Energy value Kcal |
|---|---|---|---|---|---|---|---|---|
| Dried (1) | 15.8 | 10.3 | 1.9 | 2.3 | 5.8 | 6.5 | 5.5 | 375 |
| Dried (4) | 19.5 | 26.0 | 2.9 | 5.0 | 1.5 | 13.5 | 6.1 | 345 |
| Dried (3, 4) | 18.4 | 13.1 | 1.2 | 9.2 | 4.5 | 14.7 | 6.5 | 333 |
| Fresh (3, 4) | 90.0 | 17.5 | 8.0 | 7.5 | 9.5 | 8.0 | 7.0 | 387 |
| Fresh (2) | 91.8 | 13.4 | 4.9 | 8.0 | 0.7 | 7.3 | 3.7 | 392 |

(1) - Singer (1961)
(2) - Agrofoods Organization (1972)
(3) - Soweda (1965)
(4) - Adriano and Gruz (1933)

*Lentinus edodes* contains 17.5% of its dry weight in proteins and virtually all the essential amino acids. Approximately 25-35% of the total amino acids are free amino acids, the remainder being protein-bound. In addition to the common amino acids, rare amino acids or nitrogenous substances such as: β-alanine, methionine sulphoxide, cysteic acid, hydroxyproline, hydroxylysine, α-aminoadipic acid, α, β and γ-aminobutyric acid, pipecolic acid and 5-hydroxypipecolic acid, phosphoserine, cystathione, canavanine, creatinine, citrulline, amithine, glucosamine and ethanolamine have been detected in these mushrooms.

Amino acid composition of *Lentinus edodes* according to Kagawa (1970), Sawada (1965), Sugimosi et al. (1971)

| Amino acid | mg of amino acids per gram of crude protein. |
|---|---|
| Isoleucine | 218 |
| Leucine | 348 |
| Lysine | 174 |
| Methionine | 87 |
| Phenylalanine | 261 |
| Cystine | not determined |
| Tyrosine | 174 |
| Threonine | 261 |
| Tryptophan | not determined |
| Valine | 261 |
| Arginine | 348 |
| Histidine | 87 |
| Alanine | 305 |
| Aspartic acid | 392 |
| Glutamic acid | 1182 |
| Glycine | 218 |
| Serine | 261 |
| Total amino acids | 4962 |

Pentoses (xylose and ribose), methyl pentoses (rhamnose and fucose), hexoses (glucose, galactose and mannose), disaccharides (sucrose), amino sugars (glucosamine and N-acetylglucosamine), sugar alcohols (manutol and inositol), sugar acids (galacturonic and glucuronic acid), etc., are found in mushrooms of the *Lentinus* genus. Mannitol is present at a high concentration (9-13%).

The *Lentinus* mushroom contains polysaccharides and chitin (polymer of N-acetylglucosamine). Similarly, α,α'-trehalose, commonly known as mushroom sugar, is found.

The vitamins that are most widespread in the shii-take mushroom are thiamine, riboflavin, niacin and biotin. Vitamin A (retinol) is not usually found in these mushrooms, but provitamin A, expressed in β-carotene equivalents, can sometimes be assayed. Similarly, vitamin D is rare, but ergosterol, which can be converted to vitamin D by ultraviolet irradiation, is found.

SUMMARY OF THE INVENTION

The applicant has developed novel polysaccharide extracts derived from mushrooms of the *Lentinus* genus, which constitute the subject of the invention.

A subject of the invention is also the method for obtaining this extract.

Another subject consists of the uses of this extract as a nutraceutical or cosmetic composition or as a medicament.

Other subjects will emerge on reading the description, the drawings and the examples which follow.

BRIEF DESCRIPTION OF THE DRAWINGS

FIGS. 5a and 5b show the detection of claudin, FIGS. 6a and 6b show the detection of occludin-1, and FIGS. 7a and 7b show the detection of ZO-1. FIGS. 5a, 6a and 7a are the negative controls for the immunolabelling experiments carried out. FIGS. 5b, 6b and 7b are the result of the experiments in the presence of the polysaccharide extract according to the invention diluted to 0.1% in cell culture medium.

DETAILED DESCRIPTION OF THE ILLUSTRATIVE EMBODIMENTS

The polysaccharide extract derived from a mushroom of the *Lentinus* genus, in accordance with the invention, comprises monosaccharides, polysaccharides, and by weight, from 2% to 8% of trehalose, from 1% to 4% of glucose and from 30% to 60% of alditols, relative to the total weight of the dry extract.

Preferably, this extract comprises, in addition to the monosaccharides and the polysaccharides, from 2% to 6% of trehalose, from 2% to 3% of glucose and from 45% to 55% of alditols by weight, relative to the total weight of the dry extract. More preferably, this extract comprises, in addition to the monosaccharides and the polysaccharides, from 3% to 5% of trehalose, from 2% to 3% of glucose and from 45% to 50% of alditols by weight, relative to the total weight of the dry extract.

Preferably, the alditols contained in this extract according to the invention comprise arabinitol and mannitol.

Figure 1:
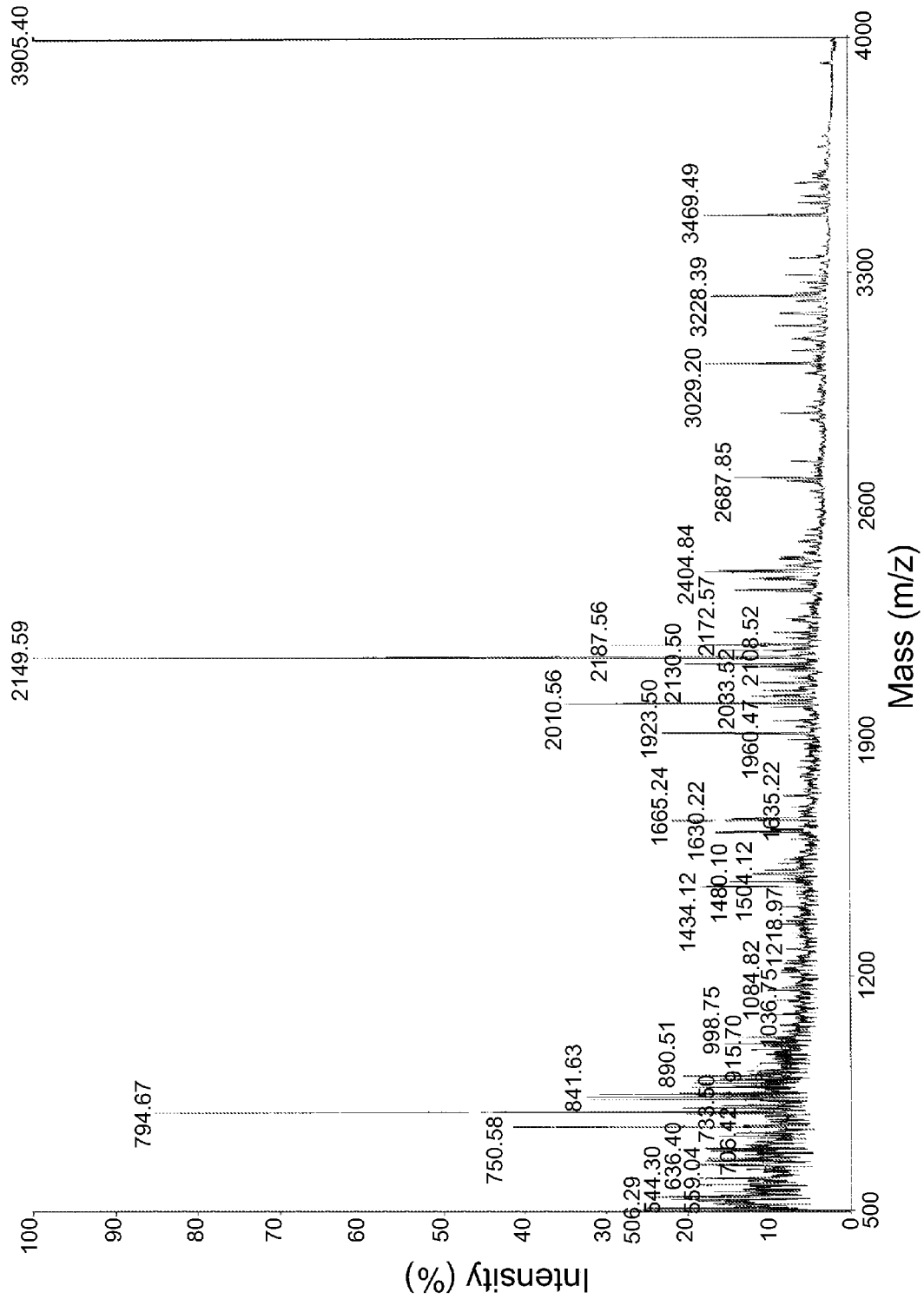
FIGS. 1 and 2 show a mass spectrometry analysis (MALDI-TOF) of the polysaccharide extract obtained in Example 1. The molecular weights of the compounds visualized rise in tiers from 500 to 10 000 m/z (mass/charge).
Figure 2:
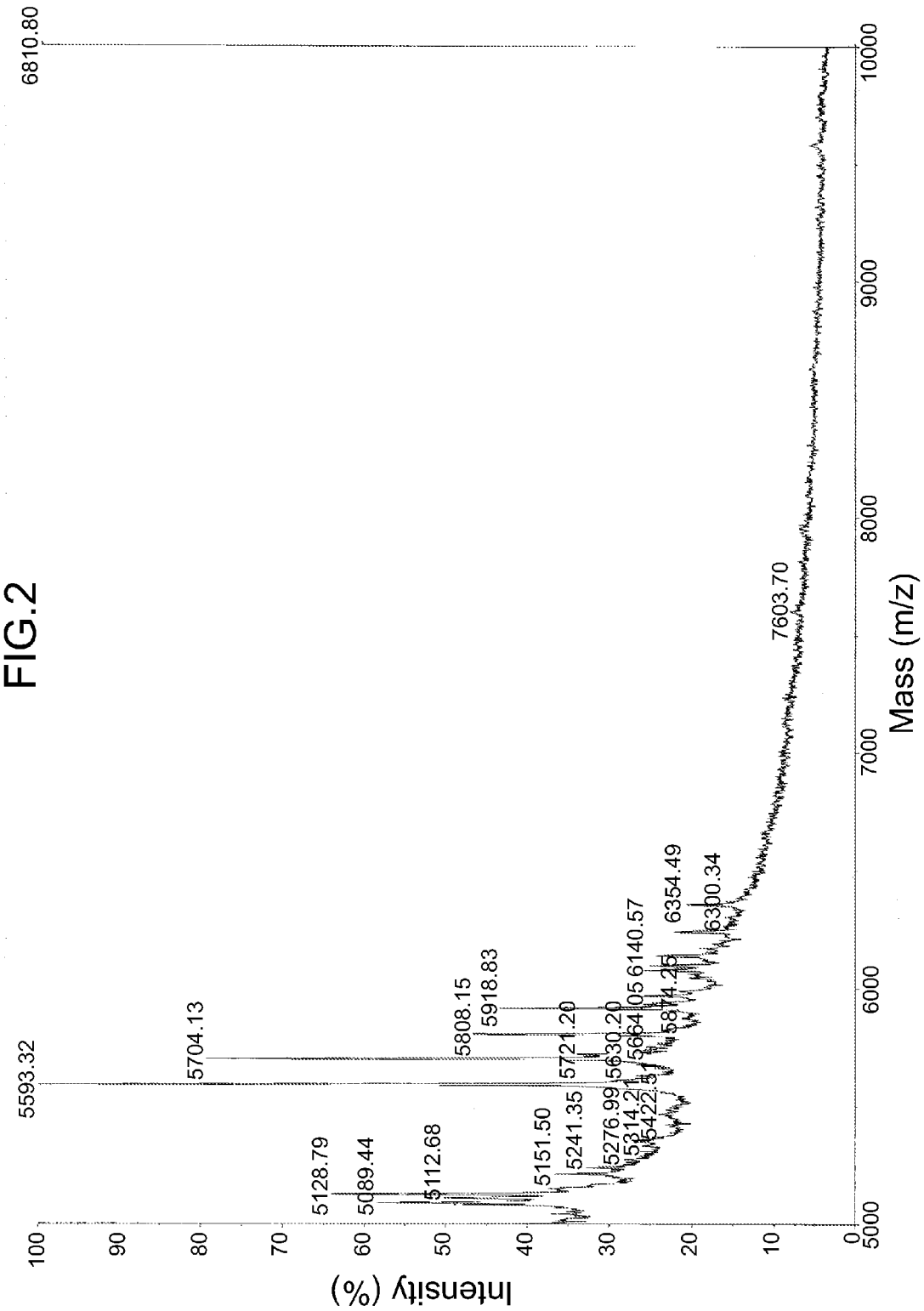

A particularly preferred polysaccharide extract is defined by the mass spectrometry analyses of FIGS. 1 and 2.

The extract according to the invention may be in powder form.

The extraction method for the selective extraction of a polysaccharide extract derived from *Lentinus* according to the invention is characterized in that one or more solid/liquid extractions are carried out, the liquid extract is precipitated with an organic solvent, centrifuged and filtered, and then the precipitate is subsequently dried so as to obtain the polysaccharide extract.

In one embodiment of this method, the extraction(s) is (are) carried out with boiling water. Preferably, the organic solvent used is ethanol.

The extracts are obtained using the previously described method from mushrooms of the *Lentinus* genus, which can be used dried. In general, the fresh mushrooms contain 85% to 95% of water and the air-dried mushrooms contain between 5% and 20% of water. Preferably, the mushrooms are *Lentinus edodes*, otherwise known as lentinula edodes, oak mushroom, shii-take, shiitake, *Cortinellus* shii-take or *Cortinellus edodes*. The name *Cortinellus* shii-take was the name most commonly used, but Singer (1941) called into question whether the shii-take belonged to the *Cortinellus* genus. Since then, the correct scientific name *Lentinus edodes* (Berk) Sing has been used. Similarly, in the former classification system, the shii-take belonged to the family Agaricaceae, whereas the modern classification system places *Lentinus edodes* in the family Tricholomataceae.

The polysaccharide extract according to the invention acts on the expression of the adhesion proteins known as tight junctions, in particular occludin, claudin and JAM (junctional adhesion molecule).

A subject of the invention is also pharmaceutical, cosmetic or nutraceutical compositions comprising such a polysaccharide extract and, optionally, a physiologically acceptable inert carrier, for the treatment of human beings or of mammals suffering from a condition or a disease related to the absence or to an excessive or pathological degradation of the adhesion proteins.

The invention thus relates to pharmaceutical compositions comprising such a polysaccharide extract, for treating dermatosis such as psoriasis, atopic dermatitis or ichthyosis.

The invention also relates to cosmetic or nutraceutical compositions comprising such a polysaccharide extract and, optionally, a physiologically or cosmetically acceptable inert carrier, for the treatment of lesions of the skin and of the mucous membranes due to ageing, such as the lesions caused by the action of solar radiation, actinic ageing, outside attacks such as the harmful effects of tobacco or pollution, for example, and the consequences of these attacks.

The polysaccharide extract according to the invention can be incorporated into or formulated in a polymeric carrier or a delivery system for topical or local use, as in the case of the treatment of a periodontal disease, to be delivered directly into the periodontal pocket.

Such compositions can be used by way of prevention or cure.

The compositions according to the invention can be ingested or applied to the skin or cutaneous surface of an individual. According to the method of administration, the composition according to the invention may be in any of the forms normally used in cosmetics or nutraceutics or as a medicament. These compositions may in particular be formulated in the form of tablets, gel capsules, capsules, ointments, creams, milks or gels.

The following examples illustrate the invention without limiting it in any way.

EXAMPLE 1

Total Aqueous and Alcohol-Precipitated Extracts 1 kilogram of dried *Lentinus edodes* is ground in a Henry knife mill. The powder obtained is extracted with 3×10 litres of boiling distilled water. The mixture is stirred for 30 minutes at 90° C. and filtered through a 50-litre Büchner filter over a layer of filtration adjuvant (celite). The mixture is concentrated to 5 litres in a Luwa thin layer evaporator, and then lyophilized in a Serail lyophilizer. An aliquot portion of each aqueous extract is dissolved in distilled water and precipitated by adding 1.5 volumes of 96° ethanol. The mixture is left in a cold room overnight and centrifuged (IEC Centra 7R). The product is dried in a desiccator under vacuum.

EXAMPLE 2

Analysis of the Extract According to the Invention by Mass Spectrometry

The extract of Example 1 was analysed by mass spectrometry (MALDI-ToF). MALDI (Matrix Assisted Laser Desorption Ionization) is a method of ionization for analysing molecules of which the molecular weight is greater than 1000 Da. The analyser coupled to the MALDI source is a time of flight (ToF) analyser which is well suited to pulsed laser desorption ionization. Separation in a time of flight analyser is based on the fact that ions of different mass, accelerated at a uniform kinetic energy, have different speeds, and therefore a different time of flight for covering a given distance.

FIGS. 1 and 2 show a visualization of all the compounds of which the molecular weights are between 500 and 10 000 m/z.

EXAMPLE 3

Characterization of the Extract of Example 1 by Chromatography

Figure 3:
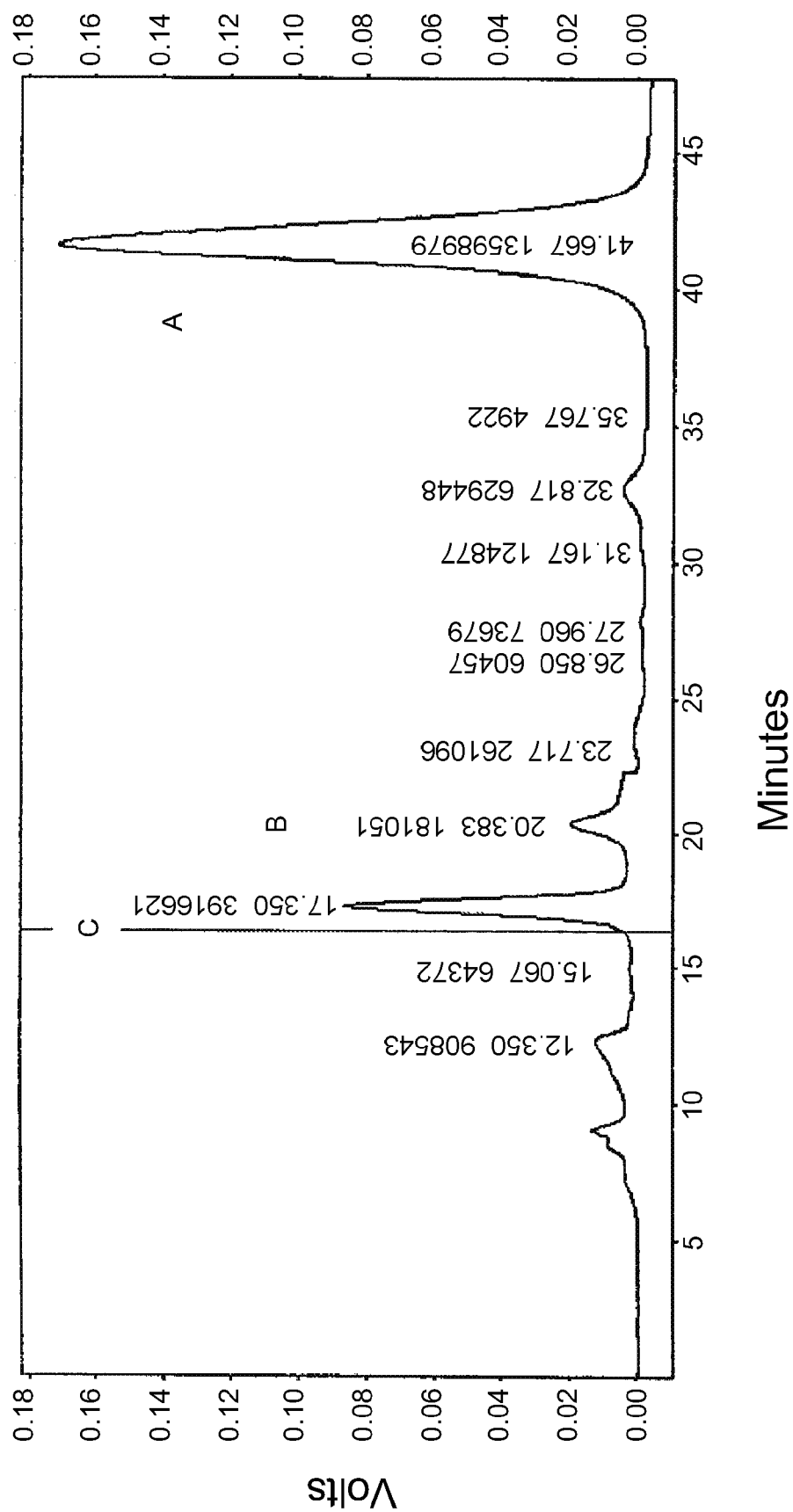
FIGS. 3 and 4 show chromatographic analyses of the polysaccharide extract obtained in Example 1. The analysis summarized in FIG. 3 was carried out on ion exchange liquid chromatography. That of FIG. 4 is a size exclusion chromatography.

The analysis of the crude extract of Example 1 was carried out by ion exchange liquid chromatography on a CARBO-Sep column (CHO-682, Interchim), the unique selectivity of which allows the separation of mono- and disaccharides using only pure water as eluent. The chromatogram obtained (FIG. 3) shows the predominant presence of a small hydroxylated molecule (A) and, inter alia, two compounds that may correspond to a monosaccharide (B) and a disaccharide (C).

Figure 4:
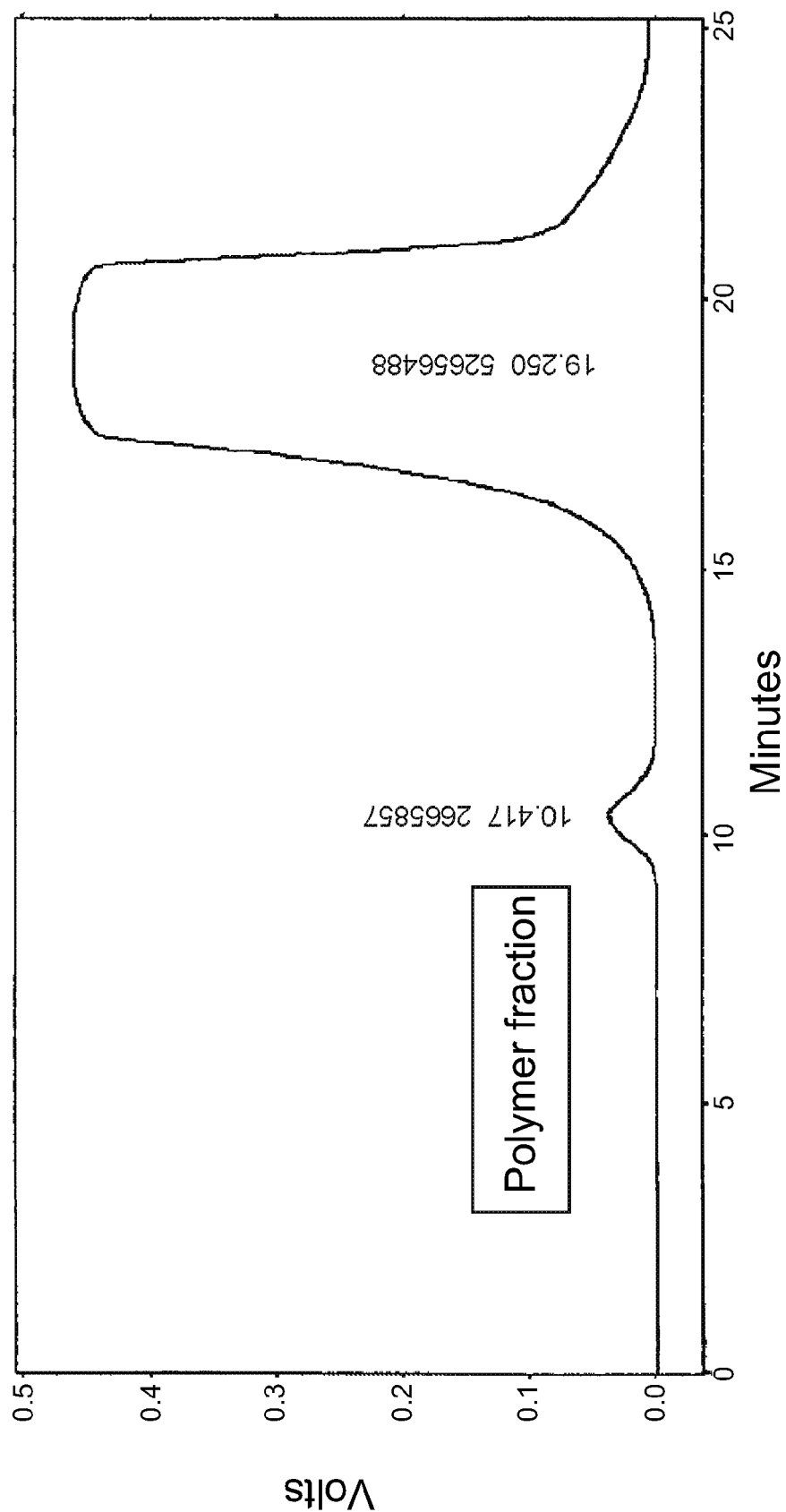

In a second step, the analysis of the crude extract was carried out using size exclusion chromatography on the Shodex OHpak B-804 column (exclusion limit: $4 \times 10^5$ kDalton). The chromatographic profile obtained shows that only 2% of the extract corresponds to polysaccharides (FIG. 4).

EXAMPLE 4

Ultrafiltrations of the Extract of Example 1

The successive ultrafiltrations of the crude extract carried out on cellulose ultrafiltration membranes (Diaflo®-Amicon Co) characterized by three cutoff thresholds of 100 kDalton (kD), 10 kD and 1 kD, resulted in 4 fractions being obtained (Lent. 100=MW>100 kD; Lent. 10=10 kD<MW<100 kD; Lent. 1=1 kD<MW<10 kD and Lent. UF=MW<1 kD), the content by weight of which is given below.

For each step, the washing with distilled water is considered to be complete when 10 volumes of liquid have passed through the membrane.

TABLE 1

| Fractions | Lent. 100 | Lent. 10 | Lent. 1 | Lent. UF |
|---|---|---|---|---|
| Weight (mg) | 47 | 127 | 24 | 1874* |
| % | 2.4 | 6.5 | 1.2 | 89.9 |

*After correction of the water content

The fractions containing polysaccharides, Lent. 100 and Lent. 10 correspond to 8.9% (2.4%+6.5%) of the total weight of the active extract.

Total acid hydrolysis of 4 ultrafiltrates followed by analysis of the sugars by liquid phase chromatography was used to determine the nature of the carbohydrate components. The Lent. UF fraction, the most predominant component of the extract (89.9%), contains, apart from the monosaccharides (glucose, fucose, arabinose, mannose, xylose, arabinitol, mannitol) and disaccharides (trehalose), amino acids, vitamins and minerals.

The sugar compositions of fractions Lent. 1, Lent. 10 and Lent. 100 is given in Table 2.

TABLE 2

| | Neutral-sugar composition of the fractions | | | | | | | |
|---|---|---|---|---|---|---|---|---|
| | Neutral sugars | | | | | | | |
| | Rhamnose | Fucose | Ribose | Arabinose | Xylose | Mannose | Galactose | Glucose |
| Lent. 1 | 12.3 | 10.4 | 5.2 | 2 | 2.6 | 20 | 32.5 | 15 |
| Lent. 10 | 12.6 | 5.3 | 15.4 | 1.3 | 4.5 | 21 | 13.8 | 26.1 |
| Lent. 100 | 4 | 5.1 | 7.1 | 5.4 | 4.6 | 17.1 | 26.4 | 29.3 |

* calculated on all the neutral sugars identified

All the results obtained following the various analyses of the active extract of Example 1 are given in Table 3.

EXAMPLE 5

Demonstration of the Action of an Extract of Shii-Take on Hydration of the Skin

The expression of the structural proteins of the tight junctions (claudin, occludin, ZO-1) was evaluated by the immunohistochemistry technique in control keratinocytes or keratinocytes treated with the extract of shii-take.

HaCaT human keratinocytes (German Cancer Research Centre, Heidelberg, Germany) were cultured in an incubator (37° C., 5% $CO_2$) in DMEM Glutamax medium (Invitrogen, GIBCO, cat No. 61965) with 10% FCS. At $D_0$, $8 \times 10^3$ cells are seeded onto Lab-Tek slides (VWR International S.A.S., Nalge Nunc International, cat No. 177445), and then returned to the incubator. At $D_3$, the culture medium is replaced with the extract of shii-take according to Example 1, diluted to 0.1% in culture medium, and the slides are then returned to the incubator.

After incubation for 16 h in the presence of the extract tested, the cells are fixed with 4% formaldehyde and permeabilized with 0.1% Triton. The slides are then incubated for 2 h at ambient temperature in the presence of one of the primary antibodies for labelling the tight junctions:

rabbit anti-occludin antibody (Invitrogen, Zymed Laboratories, cat. No. 71-1500) dilution 1:35, in PBS containing 1% of BSA;

rabbit anti-claudin-1 antibody (Invitrogen Zymed Laboratories, cat. No. 51-9000) dilution 1:35, in PBS containing 1% of BSA;

rabbit anti-ZO-1 antibody (Invitrogen Zymed Laboratories, cat. No. 61-7300) dilution 1:90, in PBS containing 1% of BSA.

After washing, a second incubation for 2 h is carried out with a solution of PBS with 1% of BSA containing a goat anti-rabbit antibody conjugated to AlexaFluor 488 (Invitrogen, Molecular Probes, cat No. A11008), dilution 1:200, in order to label the primary antibodies.

The slides are rinsed, and then mounted (Fluorescent Mounting Medium, Dako, cat No. S3023) and observed under a Nikon TE2000E microscope, with a×100 objective.

Figure 5B:
FIGS. 5a and 5b, 6a and 6b, and 7a and 7b show the expression of the structural proteins of tight junctions in HaCaT cells by an immunohistochemistry technique.
Figure 5A:
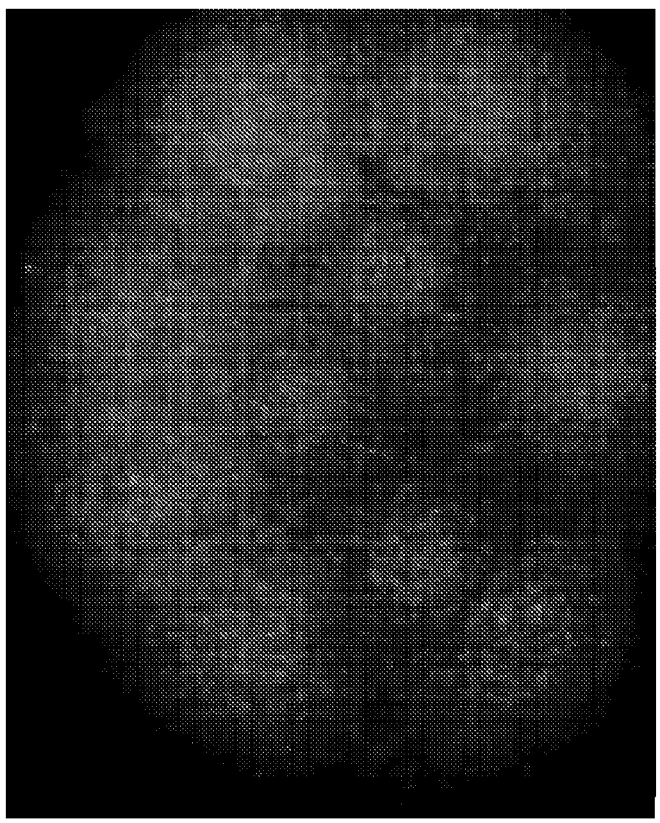
Figure 6B:
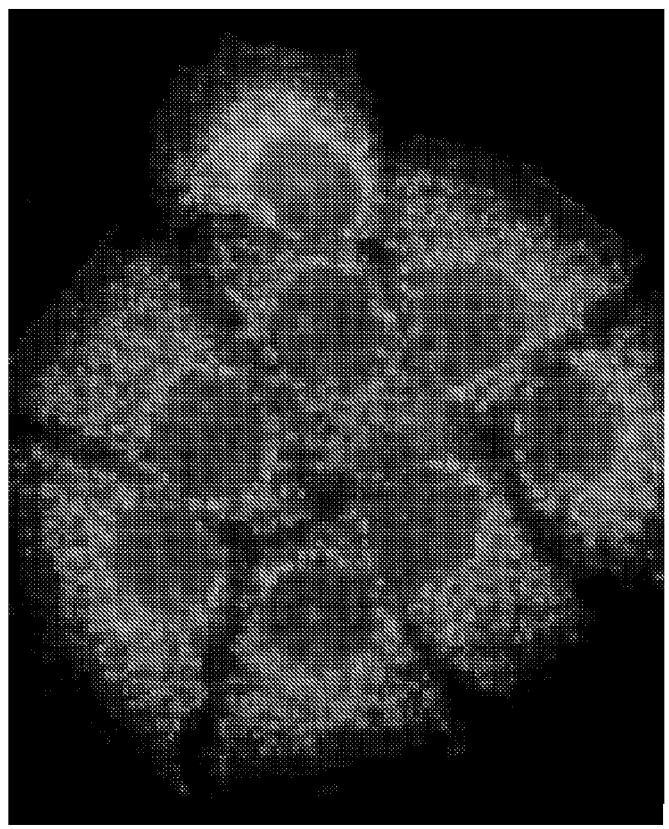
Figure 6A:
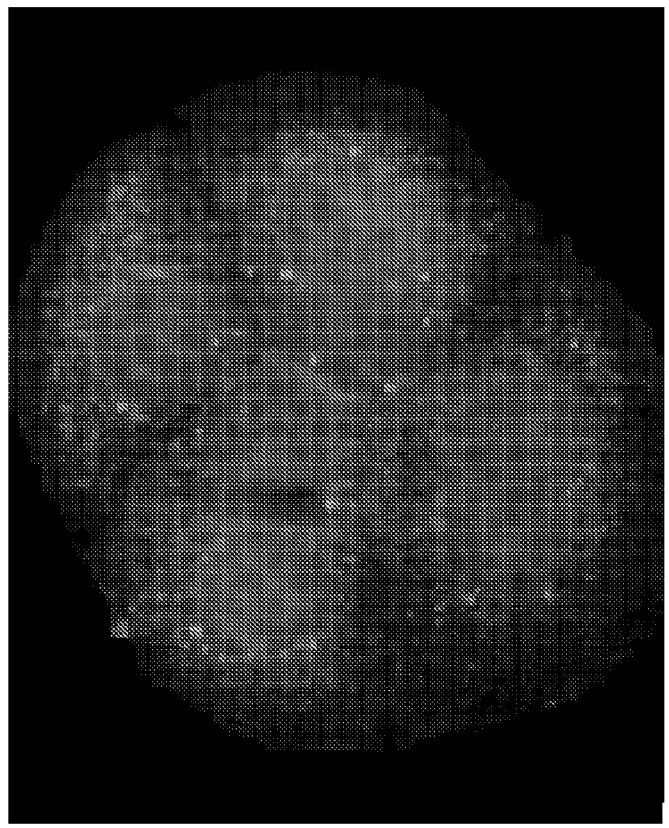
Figure 7B:
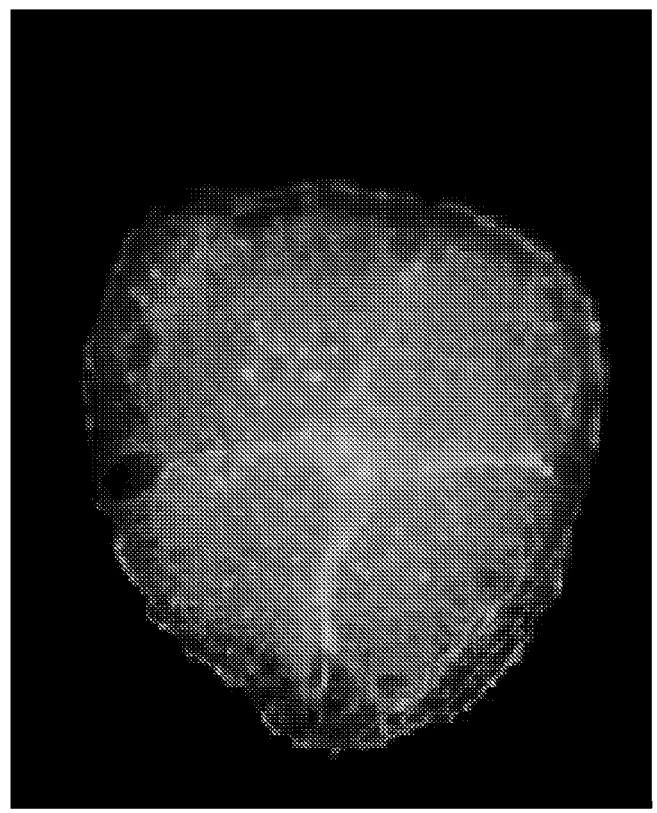
Figure 7A:
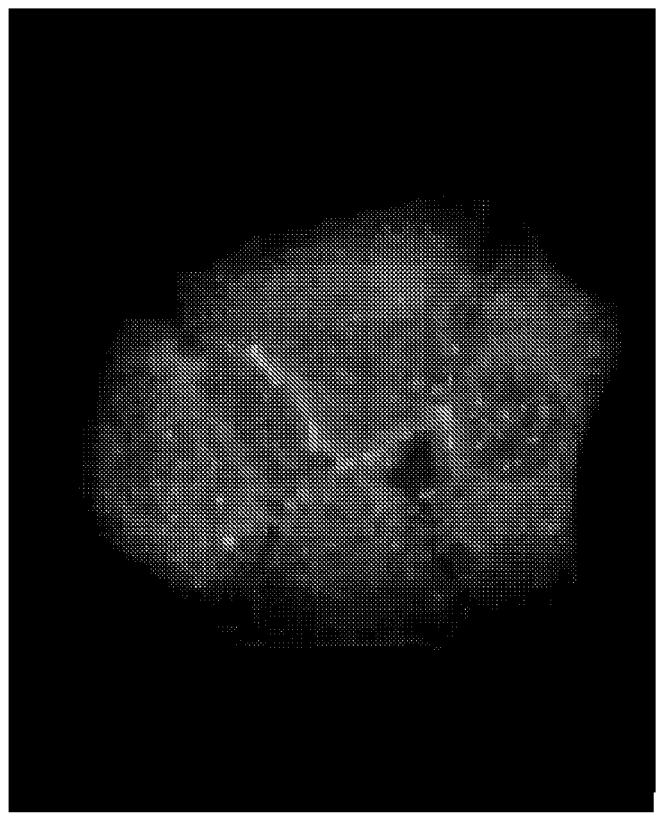

FIGS. 5, 6 and 7 show that the treatment of the keratinocytes with the ethanolic polysaccharide extract of shii-take induces a significant increase in the expression of the three proteins studied, claudin, occludin and ZO-1. Now, it is

TABLE 3

| Constituents | (Lent. 100 + Lent. 10) including polysaccharides | Fraction >1 kD | Other constituents | Trehalose | Glucose | Other monosaccharides | Alditols |
|---|---|---|---|---|---|---|---|
| As % | 8.9 | 1.2 | 34.1 | 4 | 2.6 | 2.9 | 46.3 | known that modifications of the expression of these proteins that are essential to the cohesion of epidermal cells result in modifications of the hydration of the skin (Hadj-Rabia et al., 2004, Gastroenterology, 127(5): pp 1386-90).

These results therefore show that the treatment of cells with the polysaccharide extract at 0.1% contributes to better hydration of the epidermis.

EXAMPLE 6

Lentinus-Based Nutraceutical Anti-Ageing Composition

| | |
|---|---|
| Vitamin C | 30 mg |
| Vitamin E | 10 mg |
| Selenium | 75 µg |
| Extract of green tea | 60 mg |
| Evening primrose oil | 120 mg |
| Borage oil | 120 mg |
| Grapeseed oil | 120 mg |
| Extract of hops | 60 mg |
| Extract of *Lentinus* according to Example 1 | 1 to 50 mg |

In the nutraceutical compositions of Examples 6, 7 and 8, the extract of *Lentinus* can be used alone or in a composition with other active agents (fatty acids, minerals, vitamins) in gel capsules or capsules.

EXAMPLE 7

Nutraceutical Composition for Radiance of the Complexion

| | |
|---|---|
| *Lactobacillus lactis* | 2 billion bacteria |
| *Bifidobacterium lactis* | 2 billion bacteria |
| Extract of wheat ceramide | 20 mg |
| Extract of *Lentinus* according to Example 1 | 1 to 50 mg |

EXAMPLE 8

Suntan-Activating Nutraceutical Composition

| | |
|---|---|
| Carotenoid concentrate | 25 mg |
| Vitamin E | 10 mg |
| Selenium | 75 µg |
| Lycopene concentrate | 16 mg |
| Lutein concentrate | 5 mg |
| Olive oil | 50 mg |
| Borage oil | 100 mg |
| Extract of *Lentinus* according to Example 1 | 1 to 50 mg |

EXAMPLE 9

Lentinus-Based Cosmetic Composition for "Energy Shampoo"

| INGREDIENTS | % |
|---|---|
| WATER | QS 100 |
| *ROSMARINUS OFFICINALIS* EXTRACT | 20 |
| *SALVIA OFFICINALIS* EXTRACT | 20 |
| SODIUM LAURETH SULPHATE | 8 |
| COCAMIDOPROPYL HYDROXYSULTAINE | 3 |
| PEG-4 RAPESEEDAMIDE | 2 |
| LAURYL GLUCOSIDE | 1 |
| SODIUM LAUROYL SARCOSINATE | 1 |
| PEG-200 HYDROGENATED GLYCERYL PALMATE | 0.6 |
| GLYCEROL | 0.4 |
| FRAGRANCE | QS |
| *PANAX GINSENG* EXTRACT | 0.35 |
| LACTITOL | 0.3 |
| XYLITOL | 0.3 |
| PEG-7 GLYCERYL COCOATE | 0.25 |
| PRESERVATIVES | QS |
| PEG-40 HYDROGENATED CASTOR OIL | 0.19 |
| DENAT. ALCOHOL | 0.15 |
| *LENTINUS EDODES* | 0.02 to 5 |
| *ZANTHOXYLUM ALATUM* | 0.01 |

EXAMPLE 10

Lentinus-Based Cosmetic Composition for Hair Lotion

| INGREDIENTS | % |
|---|---|
| WATER | QS 100 |
| DENAT. ALCOHOL | 29 |
| GLYCEROL | 6 |
| *CANANGA ODORATA* OIL | 1.2 |
| *CITRUS MEDICA LIMONUM* OIL | 1.2 |
| FRAGRANCE | 1 |
| *MELALEUCA LEUCADENDRON* | 0.6 |
| *ROSMARINUS OFFICINALIS* OIL | 0.6 |
| *SALVIA OFFICINALIS* OIL | 0.6 |
| *CUPRESSUS SEMPERVIRENS* | 0.45 |
| *SERENOA SERRULATA* | 0.2 |
| PRESERVATIVES | QS |
| *VITIS VINIFERA* SEED EXTRACT | 0.1 |
| SODIUM MANNURONATE METHYLSILANOL | 0.06 |
| *LENTINUS EDODES* | 0.025 to 5 |
| ACETYL TETRAPEPTIDE-2 | 0.0001 |

EXAMPLE 11

Lentinus-Based Cosmetic Composition for a Body Milk

| Phase | Starting material/Trade name | % |
|---|---|---|
| A | OSMOSED WATER | QS 100 |
|  | GLYCEROL | 5.0 |

| Phase | Starting material/Trade name | % |
|---|---|---|
| B1 | FLUID LIQUID PETROLEUM JELLY | 5.0 |
|  | DIISOPROPYL SEBACATE | 5.0 |
|  | DIISOSTEARIC PLUROL | 0.5 |
|  | PRESERVATIVE | QS |
| B2 | ACRYLATE/C10-30 ALKYL ACRYLATE CROSSPOLYMER | 0.15 |
| B3 | PALMOTENE | 0.5 |
| C | TROMETHAMINE AT 20% | 0.9 |
| D | CITRIC ACID (SOLUTION AT 10%) | 0.1 |
| E | XANTHAN GUM | 0.2 |
| F | BUFFER SOLUTION pH 7.4 | QS |
| G | EXTRACT OF *LENTINUS* according to Example 1 | 0.2 to 10 |
| I | FRAGRANCE | QS |

Procedure:

Phases A and B are heated to around 75° C. and then phases B2 and B3 are added to phase B1. B1 + 2 + 3 is added to phase A and phase C is added. Phase D is added at a temperature of around 60° C. and the other phases are added at a temperature below 50° C.

EXAMPLE 12

*Lentinus*-Based Cosmetic Composition for a Cream

| Phase | Starting material/Trade name | % |
|---|---|---|
| A1 | GLYCERYL MYRISTATE | 5.0 |
|  | DIISOPROPYL SEBACATE | 5.0 |
| A2 | STEARYL DIMETHICONE | 1.0 |
| A3 | PALMOTENE | 0.5 |
| B1 | OSMOSED WATER | QS 100 |
|  | PROPYLENE GLYCOL | 1.0 |
|  | PRESERVATIVE | QS |
| B2 | POTASSIUM CETYL PHOSPHATE | 4.0 |
| C | CITRIC ACID (SOLUTION AT 10%) | QS pH = 6.5 |
| D | EXTRACT OF *LENTINUS* | 0.25 to 10 |
| F | FRAGRANCE | QS |

Procedure:

Phases A1 and B1 are heated to around 75° C. Phases A2 and A3 are added to phase A1 and phase B2 is added to phase B1. After stirring, phase B is added to phase A. Phase C is added at a temperature below 60° C., followed by phase D. The other phases are added at a temperature below 50° C.

The invention claimed is:

1. An extract derived from a mushroom of the *Lentinus* genus comprising monosaccharides, polysaccharides, and by weight, from 2% to 8% of trehalose, from 1% to 4% of glucose and from 30% to 60% of alditols, relative to the total weight of the dry extract prepared by a method comprising:

performing at least one extraction on mushrooms of the *Lentinus* genus comprising boiling the mushrooms in distilled water to obtain a liquid extract and stirring the liquid extract for about 30 minutes at about 90° C.;

treating the liquid extract with an organic solvent to form a precipitate;

centrifuging and filtering the precipitate; and drying the precipitate to obtain the extract.

2. The extract of claim 1, further comprising, by weight, from 2% to 6% of trehalose, from 2% to 3% of glucose, and from 45% to 55% of alditols, relative to the total weight of the dry extract.

3. The extract of claim 1, further comprising, by weight, from 3% to 5% of trehalose, from 2% to 3% of glucose and from 45% to 50% of alditols, relative to the total weight of the dry extract.

4. The extract of claim 1, wherein the alditols comprise arabinitol and mannitol.

5. The extract of claim 1, further defined as being in powder form.

6. An extract derived from a mushroom of the *Lentinus* genus comprising monosaccharides, polysaccharides, and by weight, from 2% to 8% of trehalose, from 1% to 4% of glucose and from 30% to 60% of alditols, relative to the total weight of the dry extract having the mass spectrometry analyses of FIGS. 1 and 2.

7. The extract of claim 1, further defined as comprised in a nutraceutical, cosmetic, and/or medicament composition.

8. A nutraceutical, cosmetic, and/or medicament composition comprising an extract of claim 1.

* * * * *